United States Patent [19]
Garland

[11] Patent Number: 5,461,072
[45] Date of Patent: Oct. 24, 1995

[54] USE OF ARYL HYDROXYUREA COMPOUNDS FOR THE TREATMENT OF ATHEROSCLEROSIS

[75] Inventor: Lawrence G. Garland, Beckenham, England

[73] Assignee: Burroughs Wellcome Co., Research Triangle Park, N.C.

[21] Appl. No.: 325,941

[22] Filed: Oct. 17, 1994

Related U.S. Application Data

[63] Continuation of Ser. No. 969,201, Feb. 1, 1993, abandoned.

[30] Foreign Application Priority Data

Aug. 8, 1990 [GB] United Kingdom ............... 9017351
Aug. 2, 1990 [WO] WIPO ................ PCT/GB91/01320

[51] Int. Cl.$^6$ .................................................. A01N 43/06
[52] U.S. Cl. ..................... 514/438; 514/412; 514/415; 514/443; 514/461; 514/595; 549/58
[58] Field of Search .................... 514/438, 412, 514/415, 443, 461, 595; 549/58

[56] References Cited

FOREIGN PATENT DOCUMENTS

0416609A2 9/1990 European Pat. Off. .

OTHER PUBLICATIONS

CA83(1):485a 1975.
CA72(7):30144d 1969.
CA72(13):65214d 1969.
Hill, P.: et al. Proc. Soc. Exp. Biol. Med. 148(1) 41–9 1975.

*Primary Examiner*—Paul J. Killos
*Attorney, Agent, or Firm*—Nixon & Vanderhye

[57] ABSTRACT

The present invention is concerned with the use of a compound of formula (I): Ar—Y—Q, wherein Ar is either (i) furyl, thienyl, thienyl 1,1-dioxide, pyrryl, pyridyl, benzofuryl, benzothienyl, benzothienyl 1,1-dioxide, indolyl, naphthyl, quinolyl, or tetrahydronaphthyl, any of which is optionally substituted by one or more substituents independently selected from $C_{1-4}$ alkyl (which may itself optionally be substituted by one or more halogen atoms), $C_{1-4}$ alkoxy, halo, nitro, amino, carboxy, $C_{1-4}$ alkoxy-carbonyl and hydroxy, or (ii) phenyl optionally substituted by one or more substituents independently selected from phenyl (which is itself optionally substituted by one or more substituents independently selected from those optional substituents specified in (i) above) and those specified as optional substituents in (i) above, Y is $C_{1-10}$ alkylene or $C_{2-10}$ alkenylene; Q is formula (II), where $R^1$ is hydrogen, $C_{1-4}$ alkyl, a group as defined for Ar above, or a group of formula -N($R^4$)$R^5$ wherein $R^4$ is hydrogen or $C_{1-4}$ alkyl and $R^5$ is hydrogen, $C_{1-4}$ alkyl, or phenyl optionally substituted by one or more substituents independently selected from those specified as optional substituents in (i) above; and $R^2$ is hydrogen, $C_{1-4}$ alkyl, amino, $C_{1-4}$ alkylamino, di-$C_{1-4}$ alkylamino, $C_{5-7}$ cycloalkylamino, $C_{5-7}$ cycloalkyl($C_{1-4}$ alkyl)-amino, anilino, N-$C_{1-4}$ alkylanilino, or a group as defined for Ar above; or a physiologically acceptable base salt or physiologically functional derivative thereof; in the manufacture of a medicament for the prophylaxis and treatment of conditions for which inhibition of the oxidative modification of lipids is indicated, for example, atherosclerosis. The medicaments obtained thereby and their preparation and use in the prophylaxis and treatment of the aforementioned conditions are also within the scope of the invention.

3 Claims, No Drawings

USE OF ARYL HYDROXYUREA COMPOUNDS FOR THE TREATMENT OF ATHEROSCLEROSIS

This is a continuation of application Ser. No. 07/969,201, filed Feb. 1, 1993, now abandoned.

The present invention is concerned with the use of certain aryl hydroxyurea compounds in the manufacture of medicaments for the prophylaxis and treatment of clinical conditions for which inhibition of the oxidative modification of lipids is indicated, for example, atherosclerosis, with the medicaments obtained thereby and with their preparation and use in the prophylaxis and treatment of such conditions.

European Patent Specification 0279263 describes a novel class of compounds having 5- and/or 12-lipoxygenase inhibiting properties which have potential utility in the treatment of asthma, allergy, arthritis, psoriasis and inflammation.

We have now found that the compounds of EPS 0279263 also have the ability to scavenge the peroxyl radicals implicated in the oxidation of low density lipoprotein (LDL). It follows that these compounds may be suitable for use in the treatment of conditions for which inhibition of the oxidative modification of lipids is indicated, for example, atherosclerosis.

$$Ar-Y-Q \quad (I)$$

wherein

Ar is either (i) furyl, thienyl, thienyl 1,1-dioxide, pyrryl, pyridyl, benzofuryl, benzothienyl, benzothienyl 1,1-dioxide, indolyl, naphthyl, quinolyl, or tetrahydronaphthyl, any of which is optionally substituted by one or more substituents independently selected from $C_{1-4}$ alkyl (which may itself optionally be substituted by one or more halogen atoms), $C_{1-4}$ alkoxy, halo, nitro, amino, carboxy, $C_{1-4}$ alkoxycarbonyl and hydroxy, or (ii) phenyl optionally substituted by one or more substituents independently selected from phenyl (which is itself optionally substituted by one or more substituents independently selected from those specified as optional substituents in (i) above) and those, optional substituents specified in (i) above;

Y is $C_{1-10}$ alkylene or $C_{2-10}$ alkenylene;

Q is

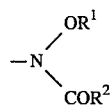

where $R^1$ is hydrogen, $C_{1-4}$ alkyl, a group as defined for Ar above, or a group of formula $-N(R^4)R^5$ wherein $R^4$ is hydrogen or $C_{1-4}$ alkyl and $R_5$ is hydrogen, $C_{1-4}$ alkyl, or phenyl optionally substituted by one or more substituents independently selected from those specified as optional substituents in (i) above; and $R^2$ is hydrogen, $C_{1-4}$ alkyl, amino, $C_{1-4}$ alkylamino, di-$C_{1-4}$ alkylamino, $C_{5-7}$ cycloalkyamino, $C_{5-7}$ cycloalkyl($C_{1-4}$alkyl)-amino, anilino, N-$C_{1-4}$ alkylanilino, or a group as defined for Ar above;

or a physiologically acceptable base salt or physiologically functional derivative thereof;

in the manufacture of a medicament for the prophylaxis and treatment of conditions for which inhibition of the oxidative modification of lipids is indicated, for example, atherosclerosis.

Preferred compounds for use in the manufacture of the medicaments of the invention include those wherein Ar is benzofur-2-yl or benzothien-2-yl;

Y is $-CH_2-$ or $-CH(Me)-$; and

Q is as hereinbefore defined, $R^1$ is hydrogen and $R^2$ is $C_{1-4}$ alkyl, amino, $C_{1-4}$ alkylamino, or di-$C_{1-4}$ alkylamino;

and physiologically acceptable base salts and physiologically functional derivatives thereof.

A particularly preferred compound for use in the manufacture of a medicament according to the invention is N-hydroxy-N-(1-benzo[b]thien-2-ylethyl)urea or a physiologically acceptable base salt or physiologically functional derivative thereof.

Physiologically acceptable salts for use in the manufacture of the medicaments of the present invention include ammonium salts, alkali metal salts, such as those of sodium and potassium, alkaline earth salts, such as those of calcium and magnesium, salts with organic bases, such as those of dicyclohexylamine and N-methyl-D-glucamine, and salts with amino acids, such as those of arginine and lysine.

The above compounds of formula (I) and their physiologically acceptable base salts and physiologically functional derivatives are hereinafter referred to as "compounds of formula (I)" in relation to the therapeutic and pharmaceutical aspects of the invention discussed below.

According to further aspects of the invention, there are provided:

(a) medicaments comprising a compound of formula (I), at least one pharmaceutically acceptable carrier and, optionally, one or more other therapeutically active compounds, for use in the prophylaxis and treatment of a condition for which inhibition of the oxidative modification of lipids is indicated, for example, atherosclerosis, and (b) methods for the prophylaxis and treatment of a condition in a mammal, such as a human, for which inhibition of the oxidative modification of lipids is indicated, for example, atherosclerosis, which comprise the administration to said mammal of a therapeutically effective amount of a compound of formula (I) as hereinbefore defined.

The amount of a medicament according to the invention required to achieve the desired therapeutic effect will, of course, vary with the particular compound of formula (I) contained therein, the route of administration, the subject under treatment and the particular disorder or disease being treated. A suitable dose for a mammal suffering from, or likely to suffer from, any of the clinical conditions described hereinbefore is in the range 0.1 μg to 500 mg of compound/ kg bodyweight. In the case of systemic administration, the dose is typically in the range 0.5 to 500 mg of compound/kg bodyweight, the most preferred dosage being 0.5 to 50 mg/kg bodyweight, for example, 5 to 25 mg/kg, administered two or three times daily.

As indicated, a medicament according to the invention comprises a compound of formula (I) in association with at least one pharmaceutically acceptable carrier and, optionally, one or more other therapeutically active compounds. The carrier must, of course, be compatible with the other ingredients in the medicament and must not be detrimental to the recipient. The compound of formula (I) may comprise from 0.1% to 99.9% by weight of the medicament. Typical unit doses of a medicament according to the invention contain from 0.1 mg to 1 g of the active ingredient.

Medicaments according to the invention include those in a form suitable for oral, pulmonary, rectal, or parenteral (including subcutaneous, intramuscular and intravenous) administration.

Medicaments according to the invention may conveniently be presented in unit dosage form and may be prepared by any method known in the art of pharmacy. All such methods include the step of bringing the compound of formula (I) into association with a carrier which may contain one or more accessory ingredients. In general, the medicaments of the invention are prepared by uniformly and intimately bringing the compound of formula (I) into association with a liquid carrier or a finely divided solid carrier, or both, and then, if desired, shaping the product into the required form, for example, by compression or moulding.

Medicaments according to the invention which are suitable for oral administration may be in the form of discrete units, such as capsules, cachets, tablets, or lozenges, each containing a predetermined amount of the compound of formula (I); in the form of a powder or granules; in the form of a solution or a suspension in an aqueous or non-aqueous liquid; or in the form of an oil-in-water or water-in-oil emulsion. The medicament may also be in the form of a bolus, electuary, or paste.

Medicaments suitable for parenteral administration typically comprise a sterile aqueous preparation of the compound of formula (I) which is preferably isotonic with the blood of the intended recipient.

In addition to the aforementioned ingredients, medicaments according to the invention may include one or more additional ingredients selected from diluents, buffers, flavouring agents, binders, surface-active agents, thickeners, lubricants, preservatives, anti-oxidants and emulsifying agents. The compounds of formula (I) may also be advantageously employed in combination with one or more other therapeutically active compounds selected, for example, from an antibiotic (for example, an anti-bacterial), anti-fungal, or anti-viral agent, an anti-histamine (particularly a peripherally-acting anti-histamine), or a non-steroidal anti-inflammatory drug (NSAID).

The compounds of formula (I) and their physiologically acceptable base salts and physiologically functional derivatives for use in the manufacture of the medicaments of the present invention may be prepared by the methods described in EPS 0279263.

For a better understanding of the invention, the following Examples are given by way of illustration.

PHARMACEUTICAL FORMULATION EXAMPLES

The "active ingredient" in the following formulations may be any compound of formula (I) as hereinbefore defined.

| Example A: Tablet | Per tablet |
|---|---|
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powder using a solution of povidone in purified water. Dry the granules, add the magnesium stearate and compress to produce tablets (100 mg per tablet).

| Example B: Injectable solution | | |
|---|---|---|
| Active Ingredient | | 10.0 mg |
| Water for Injections B.P. | to | 1.0 ml |

The active ingredient is dissolved in half of the Water for Injections and then made up to volume and sterilised by filtration. The resulting solution is distributed into ampoules under aseptic conditions.

BIOLOGICAL ACTIVITY

(i) Peroxyl radical scavenging

The ability of the compounds of the invention to scavenge peroxyl radicals was measured using the method described in Biochem. Pharm. 38, 1465 (1989) wherein the peroxidation of linoleic acid is inhibited. N-Hydroxy-N-(1-benzo[b]thien-2-ylethyl)urea was found to have significant anti-oxidant activity with an apparent rate constant ($k_{AH}$) for peroxyl radical scavenging of 0.11.

(ii) Inhibition of copper-induced peroxidation of LDL

Addition of copper to human low density lipoprotein (LDL) results in the initiation of a peroxidative reaction. This results in the formation of conjugated dienes in the lipid phase and a consequent increase in UV-absorbance at 234 nm. Chain-breaking peroxyl radical scavengers inhibit this increase in absorbance at 234 nm and this is used as the basis for an assay to estimate the ability of a compound to inhibit the peroxidation of LDL. The reaction was initiated by the addition of 10 μM $CuSO_4$ to a solution of LDL (125 μg/ml) in phosphate-buffered saline. The test compounds were added as ethanolic solutions while ensuring the ethanol content of the resulting solution did not exceed 1% v/v. The absorbance at 234 nm was monitored continuously with LDL containing 4 μM butylated hydroxytoluene (BHT) and no copper as an optical reference. The time taken for the absorbance to increase to 50% of the maximum was measured for each test compound and plotted as a function of concentration. From this plot, the concentration of compound needed to delay conjugated diene formation by 60 minutes ($I_{60}$) was calculated. N-Hydroxy-N-(1-benzo[b]thien-2-ylethyl)urea was found to significantly inhibit the peroxidation of LDL with an $I_{60}$ value of 40.1 μM.

(iii) Inhibition of endothelial cell modification of LDL

Cultured endothelial cells can modify low density lipoprotein (LDL) so that it is rapidly taken up by the macrophage scavenger receptor. The modification involves peroxidation of LDL and brings about changes in the physiocochemical properties of LDL including an increase in electrophoretic mobility. Peroxyl radical scavengers have been shown to inhibit the endothelial cell modification of LDL as determined by a decrease in the electrophoretic mobility of the sample.

Porcine aortic endothelial cells at confluence were incubated for 24 hours at 37° C. in Hams F10 medium containing 0.2 mg/ml of LDL and a range of concentrations of the test compound in ethanolic solution. The ethanol concentration was always 0.5% w/v. At the end of the incubation, the samples were concentrated and changes in the electrophoretic mobility relative to native LDL measured.

From a plot of concentration against relative electrophoretic mobility, the $IC_{50}$ (concentration of test compound required to inhibit LDL modification by 50%) was determined for each sample. N-Hydroxy-N-(1-benzo[b]thien-2-ylethyl)urea was found to significantly inhibit LDL modification with an $IC_{50}$ of 0.5 μM.

I claim:

1. A method of preventing or treating atherosclerosis comprising administering to a patient in need of same, an effective amount of a compound of formula (I)

wherein Ar is either
  (i) furyl, thienyl, thienyl 1,1-dioxide, pyrryl, pyridyl, benzofuryl, benzothienyl, benzothienyl 1,1-dioxide, indolyl, naphthyl, quinolyl, or tetrahydronaphthyl, any of which is optionally substituted by one or more substituents independently selected from $C_{1-4}$ alkyl, which may itself optionally be substituted by one or more halogen atoms, $C_{1-4}$ alkoxy, halo, nitro, amino, carboxy, $C_{1-4}$ alkoxycarbonyl and hydroxy; or
  (ii) phenyl substituted by one or more substituents independently selected from phenyl, which is itself optionally substituted by one or more substituents independently selected from those specified as optional substituents in (i) above, and those optional substituents specified in (i) above;

Y is $C_{1-10}$ alkylene or $C_{2-10}$ alkenylene;

Q is

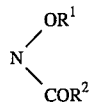

where $R^1$ is hydrogen, $C_{1-4}$ alkyl, a group as defined for Ar above, or a group of formula $-N(R^4)R^5$ wherein $R^4$ is hydrogen or $C_{1-4}$ alkyl and $R^5$ is hydrogen, $C_{1-4}$ alkyl, or phenyl optionally substituted by one or more substituents independently selected from those specified as optional substituents in (i) above; and $R^2$ is hydrogen, $C_{1-4}$ alkyl, amino, $C_{1-4}$ alkylamino, di-$C_{1-4}$ alkylamino, $C_{5-7}$ cycloalkylamino, $C_{5-7}$ cycloalkyl($C_{1-4}$ alkyl)amino, anilino, N-$C_{1-4}$ alkylanilino, or a group as defined for Ar above.

2. A method of preventing or treating atherosclerosis comprising administering to a patient in need of same, an effective amount of a compound of formula (I)

wherein

Ar is benzofur-2-yl or benzothien-2-yl;

Y is $-CH_2-$ or $-CH(Me)-$; and

Q is as shown in claim 1, $R^1$ is hydrogen, and $R^2$ is $C_{1-4}$ alkyl, amino, $C_{1-4}$ alkylamino or di-$C_{1-4}$ alkylamino.

3. A method of preventing or treating atherosclerosis comprising administering to a patient in need of same, an effective amount of N-hydroxy-N-(1-benzo[b]thien-2-yl-ethyl) urea.

* * * * *